United States Patent [19]
Shibata et al.

[11] Patent Number: 5,690,105
[45] Date of Patent: Nov. 25, 1997

[54] METHOD AND APPARATUS FOR DETERMINING A PARTICLE CRITERION AND PARTICLE ANALYZER USING THE CRITERION

[75] Inventors: Kimiyo Shibata, Kakogawa; Yoshihiro Mishima, Kobe, both of Japan

[73] Assignee: Toa Medical Electronics Co., Ltd., Hyogo, Japan

[21] Appl. No.: 674,103

[22] Filed: Jul. 3, 1996

[30] Foreign Application Priority Data

Jul. 4, 1995 [JP] Japan .................................. 7-168751

[51] Int. Cl.⁶ .................................................. A61B 5/000
[52] U.S. Cl. .................................. 128/637; 356/39
[58] Field of Search ........................ 73/865.5; 128/633, 128/664, 665, 637; 356/39, 335, 336, 338; 364/413.08, 413.1, 555

[56] References Cited

U.S. PATENT DOCUMENTS

| | | | |
|---|---|---|---|
| 5,117,357 | 5/1992 | Inoue | 364/413.08 |
| 5,187,673 | 2/1993 | Carver, Jr. et al. | 364/555 |
| 5,257,182 | 10/1993 | Luck et al. | 364/413.1 |
| 5,428,441 | 6/1995 | Ogino et al. | 356/39 |
| 5,457,526 | 10/1995 | Kosaka | 356/39 |
| 5,469,375 | 11/1995 | Kosaka | 364/555 |
| 5,548,395 | 8/1996 | Kosaka | 356/39 |

*Primary Examiner*—Jennifer Bahr
*Assistant Examiner*—Bryan K. Yarnell

[57] ABSTRACT

A method and apparatus for determining a particle criterion to set a predetermined region as the particle criterion in a distribution data of a particles of a specimen and to analyze the specimen based on particles which appear in the predetermined region, includes preparing first fundamental distribution data by accumulating each distribution data of a first specimen group which belongs to a first category, preparing second fundamental distribution data by accumulating each distribution data of a second specimen group which belongs to a second category, calculating a region on the distribution data where peculiar particles exist in the first or second category by comparing the first and second fundamental distribution data and establishing the calculated region as the particle criterion. The region may also be shifted if needed.

20 Claims, 17 Drawing Sheets

Fig.13 (a)
Fig.13 (b)
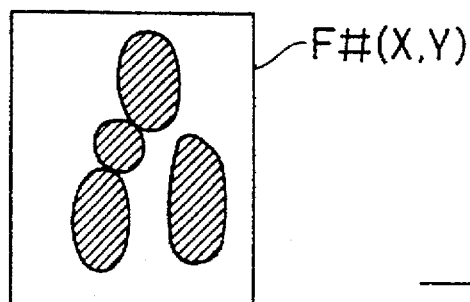
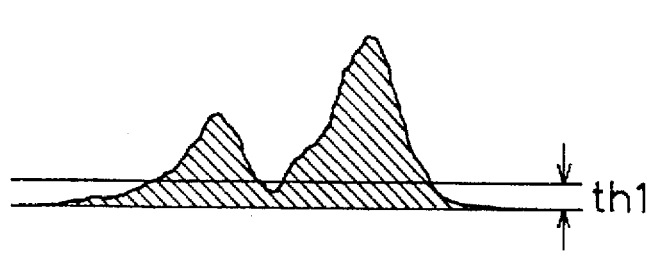
Fig.14 (a)
Fig.14 (b)
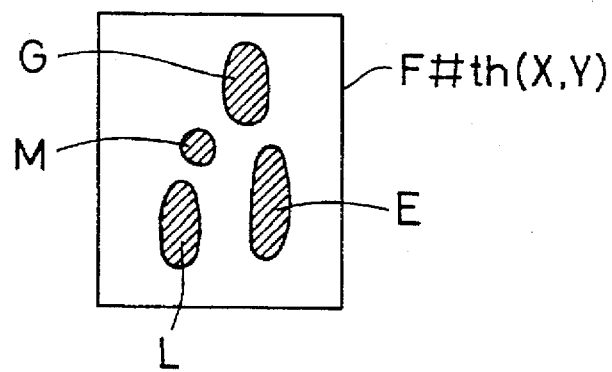
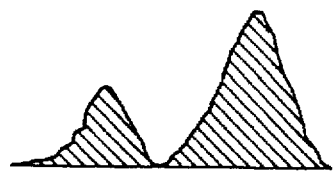

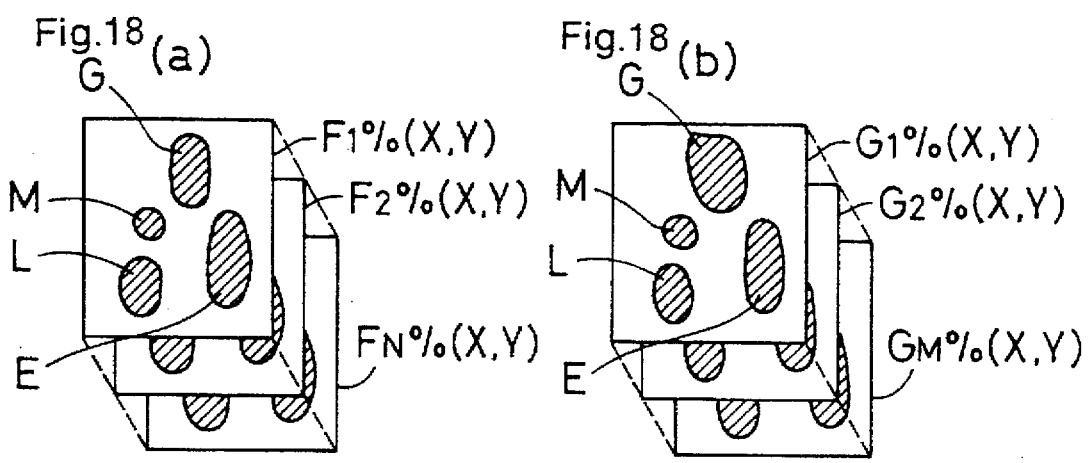
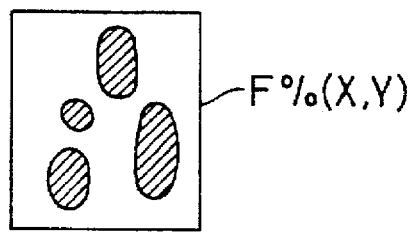
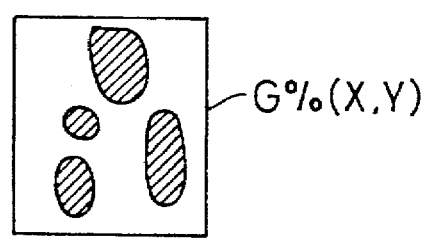

H%(X,Y)

th3

W%    I%(X,Y)

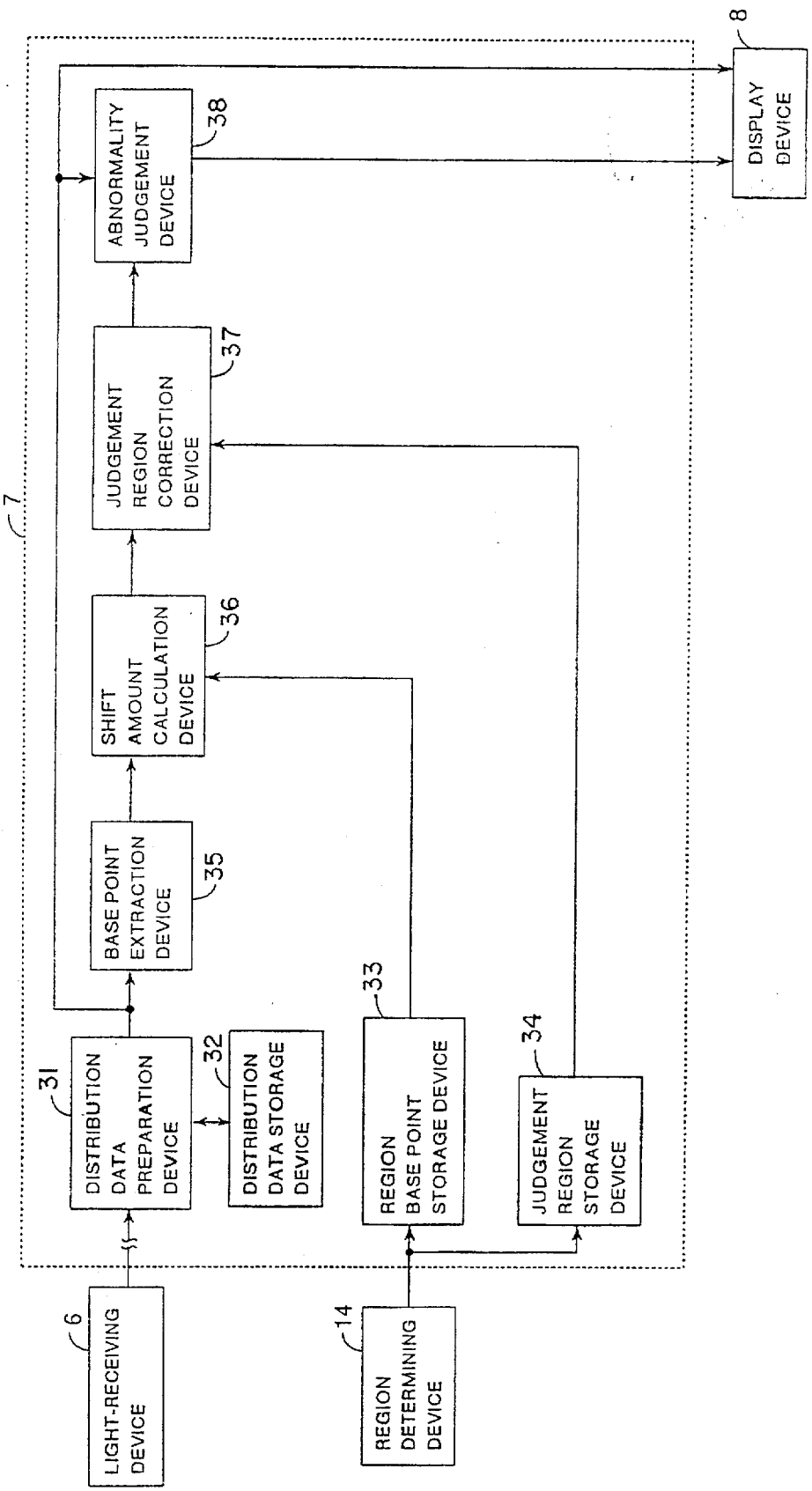

5,690,105

1

METHOD AND APPARATUS FOR DETERMINING A PARTICLE CRITERION AND PARTICLE ANALYZER USING THE CRITERION

FIELD OF THE INVENTION

The present invention relates to a particle analyzer for analyzing particles such as cells and blood corpuscles, inorganic particulates and the like, and more particularly to a method and apparatus for determining a particle criterion for discriminating abnormal blood corpuscles based on a scattergram for blood corpuscles which is prepared by measuring a specimen, and to a particle analyzer using the criterion.

DESCRIPTION OF THE BACKGROUND ART

Conventionally, a blood analyzer has been well-known wherein a scattergram for blood corpuscles included in a specimen is prepared, the number of abnormal corpuscles which appear in a judgement region that is set, in advance, as a particle criterion in the scattergram is counted and the state of the specimen is judged according to the number of the abnormal blood corpuscles so that a screening check is conducted on a lot of specimens efficiently.

However, only the skilled in hematology, reagent characteristics and the like can determine the judgement region in advance properly and easily.

SUMMARY OF THE INVENTION

In consideration of such circumstances, it is an object of the present invention to provide a method and apparatus for determining a particle criterion in which judgement regions can be determined easily without requiring skill, and a particle analyzer using the criterion.

The present invention provides a method for determining a particle criterion to set a predetermined region as a particle criterion in distribution data of particles of a specimen and to analyze the particles of the specimen based on particles which appear in the predetermined region, including the steps of preparing a first fundamental distribution data by accumulating each distribution data of a first specimen group which belongs to a first category, preparing a second fundamental distribution data by accumulating each distribution data of a second specimen group which belongs to a second category, and calculating a region on the distribution data where peculiar particles exist in the first or second category by comparing the first and second fundamental distribution data, wherein the calculated region acts as the particle criterion.

Furthermore, the present invention provides a device for determining a particle criterion to set a judgement region as a particle criterion in distribution data of particles of a specimen and to analyze the particles of the specimen based on particles which appear in the judgement region, including a first storage means for storing each distribution data of a first specimen group which belongs to a first category, a second storage for storing each distribution data of a second specimen group which belongs to a second category, a first data preparation device for preparing first fundamental distribution data by accumulating each distribution data of the first specimen group, second data preparation means for preparing second fundamental distribution data by accumulating each distribution data of the second specimen group, and a region determine means for calculating as a particle criterion a region on the distribution data where peculiar

2 particles exist in the first or second category by comparing the first fundamental distribution data with the second fundamental distribution data.

BRIEF DESCRIPTION OF THE DRAWINGS

FIGS. 13 (a) and 13 (b) are explanatory views for showing a method of determining a judgement region in the preferred example according to the present invention.

FIGS. 14 (a) and 14 (b) are explanatory views for showing a method of determining a judgement region in the preferred example according to the present invention.

FIGS. 18 (a) and 18 (b) are explanatory views for showing a method of determining a judgement region in the preferred example according to the present invention.

FIGS. 19 (a) and 19 (b) are explanatory views for showing a method of determining a judgement region in the preferred example according to the present invention.

FIG. 25 is a block diagram showing, in detail, an essential part of FIG. 1.

DESCRIPTION OF THE PREFERRED EMBODIMENTS

Figure 1:
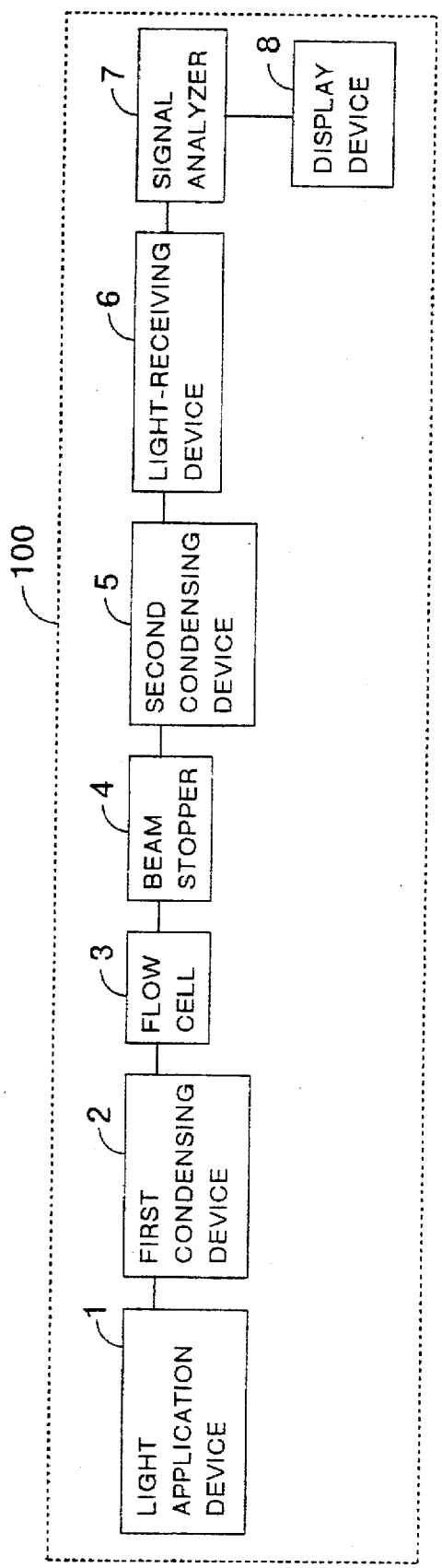
FIG. 1 is a block diagram showing a preferred example of the present invention.

Particles to be analyzed by a particle analyzer according to the present invention include various cells in body fluid, blood corpuscles, inorganic particulates and the like.

The first specimen which belongs to the first category is a specimen considered to have a parameter distributed within the predetermined range, the parameter being indicative of characteristics such as the form and size of the particles included in the specimen. An example of the first specimen is normal blood collected from a plurality of normal human bodies.

On the contrary, the second specimen which belongs to the second category is a specimen considered to have a parameter distributed also in other range than the above-mentioned predetermined range, the parameter being indicative of the characteristics such as the form and size of the particles included in the specimen. An example of the second specimen is abnormal blood collected from a human body having a particular disease (a blast cell appearing specimen, an immature granulocyte appearing specimen, a left shift specimen, an erythroblast appearing specimen or the like).

The distribution data of the particles included in the specimen represent a distribution chart based on the parameter indicative of the characteristics such as the form and size of the particles which are obtained by electrical and optical measurement (electric resistance, forward scattered light intensity, side scattered light intensity, fluorescent intensity and the like), that is, a scattergram or a histogram in order to classify the particles included in the specimen. The distribution data comprises the address and frequency of the particle in the distribution chart.

To accumulate the distribution data of a specimen group so as to prepare a fundamental distribution data means that the frequency (the number of particles) is added for each address in all distribution charts obtained from the specimen group so as to form a new distribution chart (scattergram).

A region on the distribution data where peculiar particles exist in the first or second category which is determined by a comparison between first and second fundamental distribution data may be a region on distribution data in which only one of the first and second fundamental distribution data exists, a region on the distribution data in which the ratio of the first and second fundamental distribution data is greater than a predetermined value, or both regions.

First and second storage means, first and second data preparation sections, and a region calculator can be integrally formed by using a microcomputer comprising a RAM, a ROM and a CPU.

Furthermore, the present invention provides a particle analyzer including judgement region storage for storing, as a judgement region, a region determined by an apparatus for determining the particle criterion, a distribution data preparation section for measuring a specimen to prepare the distribution data of particles included in the specimen, a judgement section for judging particles which exist in the judgement region with respect to the prepared distribution data, and an output for outputting the results of judgement obtained by the judgement means.

The judgement region storage stores, as the judgement region, the region determined by the apparatus for determining the particle criterion. The distribution data preparation section measures the specimen to prepare the distribution data. The judgement section judges the particles which exist (appear) in the judgement region with respect to the distribution data.

an for inputting optional distribution data which have already been prepared, for example, an optical disk reader may be provided in place of the distribution data preparation section. The judgement section may judge the particles which exist in the judgement region with respect to the input distribution data.

EXAMPLE

FIG. 1 shows a fundamental construction of the apparatus for analyzing particles illustrating an embodiment of the present invention. The apparatus 100 for analyzing particles comprise a flow cell 3 for letting cells flow in a line, a light application device 1 for applying laser light onto cells flowing in the flow cell 3, a light-receiving device 6 having a light-receiving sensor partitioned into at least two sections capable of detecting each of the two kinds of forward scattered light scattered by the cell, a first condensing device 2 for condensing the laser light emitted from the light application device 1 into the flow cell 3, a second condensing device 5 for condensing the two kinds of forward scattered light scattered by the cell so that the two kinds of forward scattered light are approximately parallel to the optical axis of the laser light emitted from the light application device 1, and a beam stopper 4 for stopping the passage of direct light from the light application device 1.

Also, the apparatus 100 for analyzing particles includes a signal analyzer 7 for analyzing a pulse signal of each of the two kinds of forward scattered light detected by the light-receiving device 6. The apparatus 100 for analyzing particles lets the leukocytes flow through the flow cell 3, detects the two kinds of forward scattered light with the light-receiving device 6, the two kinds of forward scattered light being scattered by the leukocytes flowing in a narrowed stream through the flow cell 3, analyzes the leukocytes with the signal analyzer 7, and displays the result of analysis with a display device 8.

Figure 2:
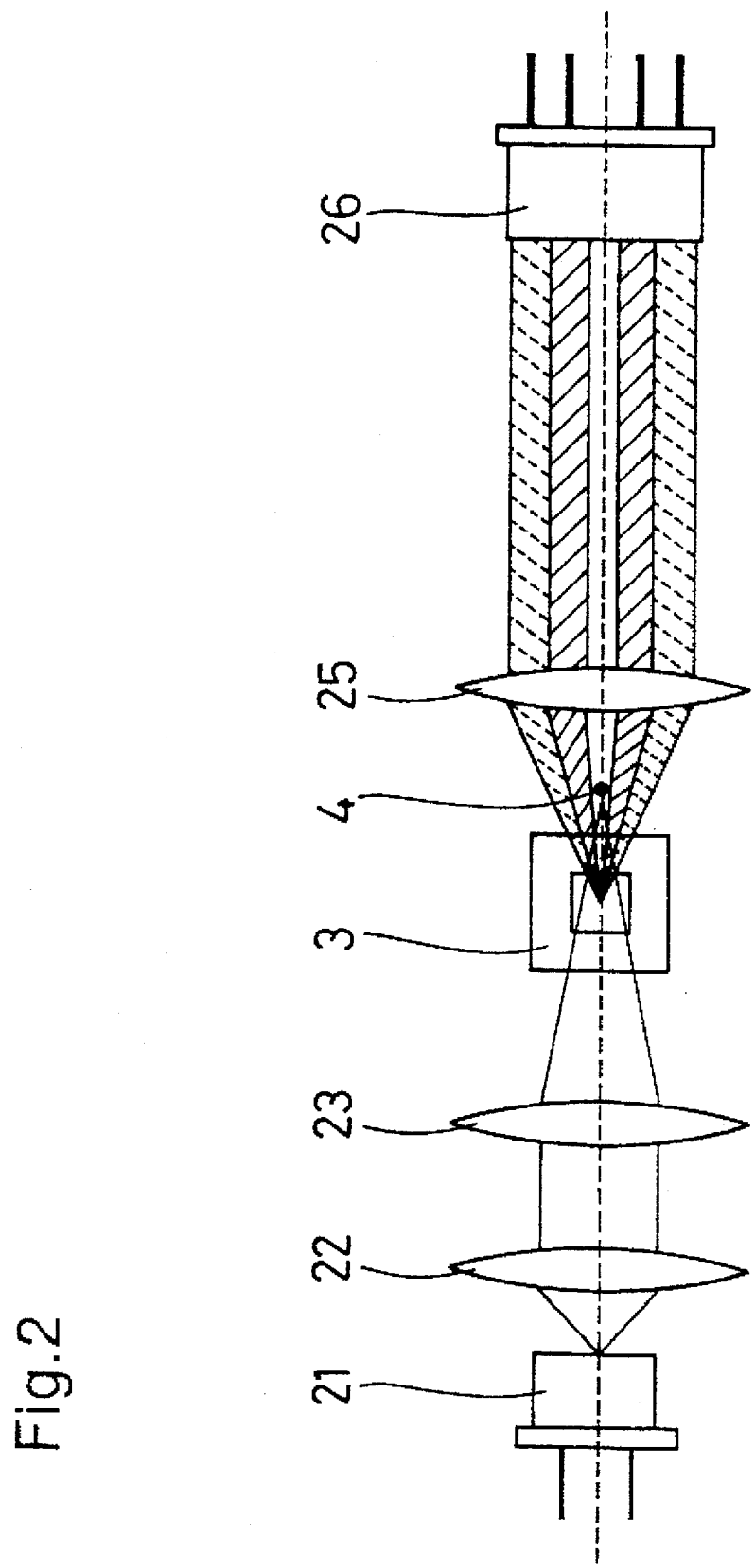
FIG. 2 is a detailed view showing an essential part of FIG. 1.

FIG. 2 is a detailed view of an essential part of FIG. 1. Referring to FIG. 2, the reference numeral 21 represents a semiconductor laser serving as the light application device 1, which may be, for example, a semiconductor laser TOLD9421 manufactured by Toshiba (with light output power 5 mW at the maximum and output wavelength 650 nm).

The first condensing device 2 includes a collimator lens 22, and 23 a condenser lens 23. The laser light emitted from the semiconductor laser 21 is condensed to a portion in the flow cell 3 where particles flow. In the flow cell 3, a blood sample processed with a reagent is narrowed into a fine stream (with a sheath flow formed), and is let to flow in a direction from the back side to the front side of the sheet of FIG. 2.

A beam stopper 4 and a collector lens 25 serving as the second condensing device 5 are disposed on the side opposite to the side where the semiconductor laser 21 is located, namely, in the rear of the flow cell 3. At some distance therefrom is disposed one photodiode 26 serving as the light-receiving device 6. The beam stopper 4 is an oblong board which extends in a direction of the stream in the flow cell for stopping the laser light (direct light) in the central portion transmitted through the flow cell 3.

The collector lens 25 is a lens for condensing the forward scattered light scattered by a cell flowing in the flow cell 3 so that the forward scattered light will be parallel to the optical axis. The collector lens 25 constitutes the second condensing device 5.

The photodiode 26 receives the forward scattered light which has been made parallel to the optical axis by the collector lens 25. Here, the photodiode has partitioned light-receiving surfaces that can receive two kinds of forward scattered light among the scattered lights.

Figure 3:
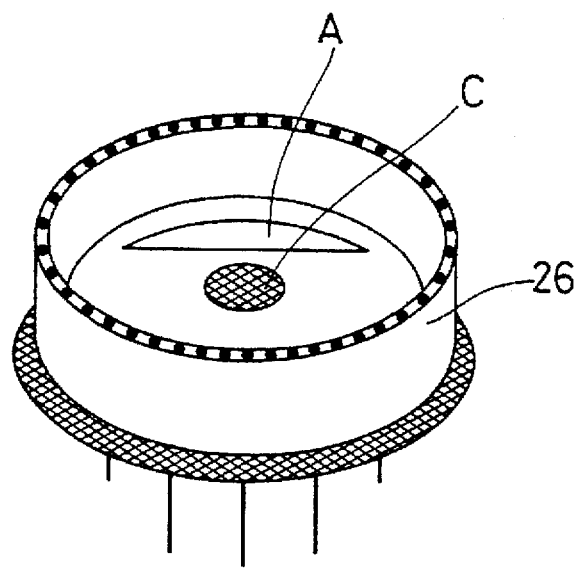
FIG. 3 is a detailed perspective view showing an essential part of FIG. 2.
Figure 4:
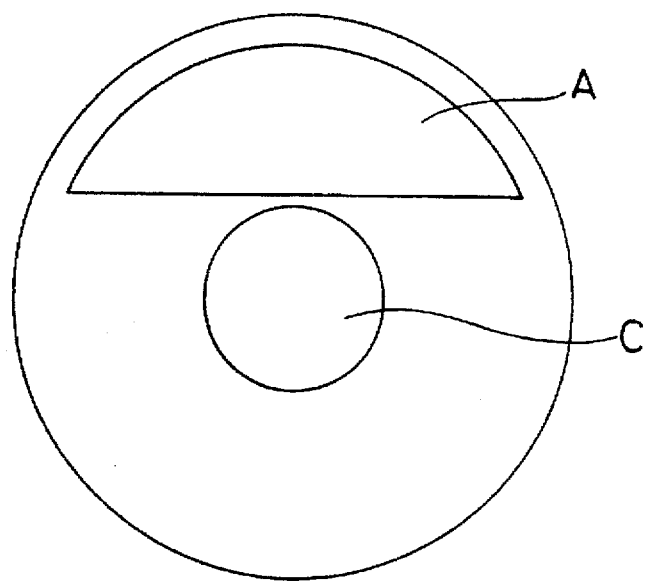
FIG. 4 is an explanatory view showing an essential part of FIG. 2.

FIG. 3 is a perspective view of the photodiode 26. FIG. 4 is an explanatory view showing the shape of the light-receiving surface.

The photodiode 26 comprises a circular light-receiving surface C in the central portion, and a semi-circular light-receiving surface A in the peripheral portion, as shown in FIG. 4.

The photodiode 26 detects a low-angle forward scattered light with an angle of 1° to 5° relative to the optical axis and a high-angle forward scattered light with an angle of 6° to 20° relative to the optical axis with the light-receiving surface C and the light-receiving surface A, respectively.

The low-angle forward scattered light reflects the size of the cell, whereas the high-angle forward scattered light reflects the inner morphology of the cell. Analysis of the signals obtained from these scattered lights makes it possible to count and classify the cells.

Here, the circular light-receiving surface C is formed to have, for example, a diameter of 1.5 mm, and the semi-circular light-receiving surface A is formed, for example, as a part of a circle having a diameter of about 6 mm.

The photodiode 26 is housed in a metal can-type vessel shown in FIG. 3 in the same manner as a photodiode usually used, and comprises several terminals for outputting electric pulse signals corresponding to the intensities of the scattered lights received.

These terminals are connected to a signal analyzer 7 as shown in FIG. 1. The signal analyzer 7 is constructed with an amplifier circuit, a peak detector circuit, an A/D converter circuit, a microcomputer, and the like. The microcomputer comprises a CPU, a ROM, a RAM, and the like. An input device such as a key board or a mouse is connected to the microcomputer depending on the needs. The display 8 is constructed with a CRT, a LCD, a printer, or the like.

The electric pulse signals output from the photodiode 26 are two kinds of signals corresponding to the light intensities of the low-angle forward scattered light and the high-angle forward scattered light, and are output for each cell passing through the region in the flow cell 3 irradiated with light.

On receiving the above electric pulse signals, the signal analyzer 7 measures the peak value, the pulse width, the area of the pulse waveform, and the like of the pulse to derive data necessary for cell analysis, thereby counting and classifying the cells.

Figure 5:
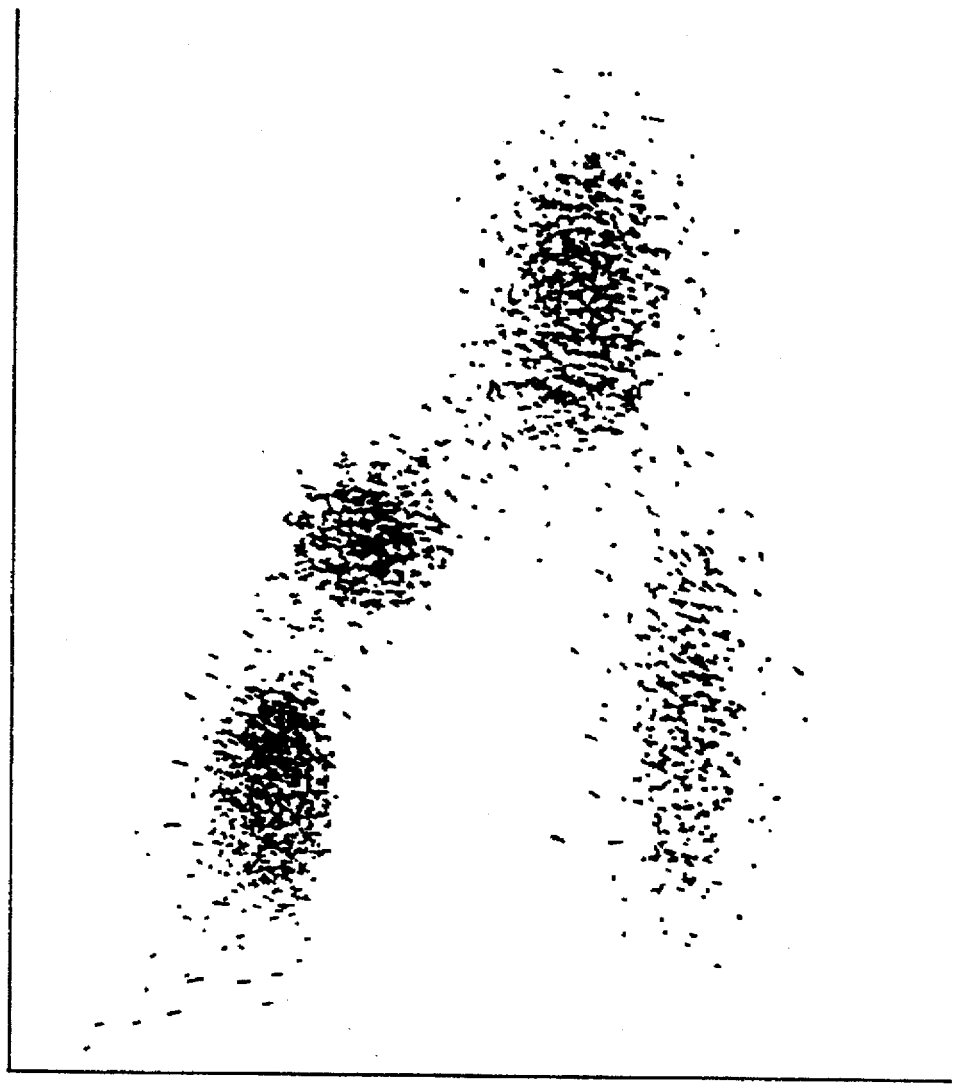
FIG. 5 is a view showing an example of a scattergram prepared in the preferred example according to the present invention.

FIG. 5 shows an example of a distribution, namely a scattergram, displayed when leukocytes are classified in the apparatus 100 for analyzing particles.

Here, the lateral axis (X axis) represents the intensity IH of the high-angle forward scattered light pulse, whereas the vertical axis (Y axis) represents the intensity IL of the low-angle forward scattered light pulse.

Figure 6:
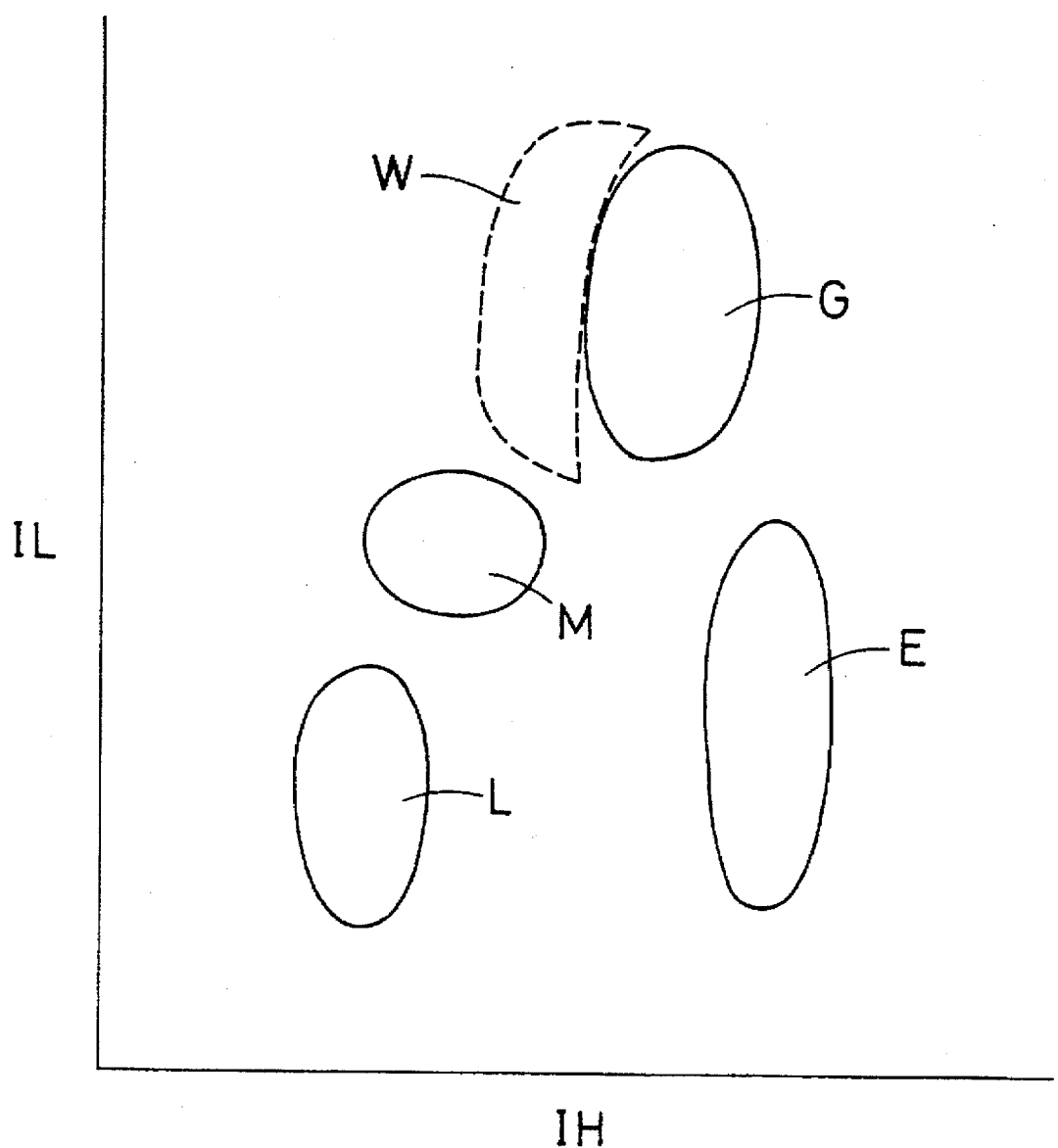
FIG. 6 is an explanatory view showing a group in FIG. 5.

In this scattergram, leukocytes are classified into four groups, as shown in FIG. 6, with lymphocytes being classified as group (cluster) L, monocytes as group M, granulocytes other than eosinophils as group G, and eosinophils as group E.

Figure 7:
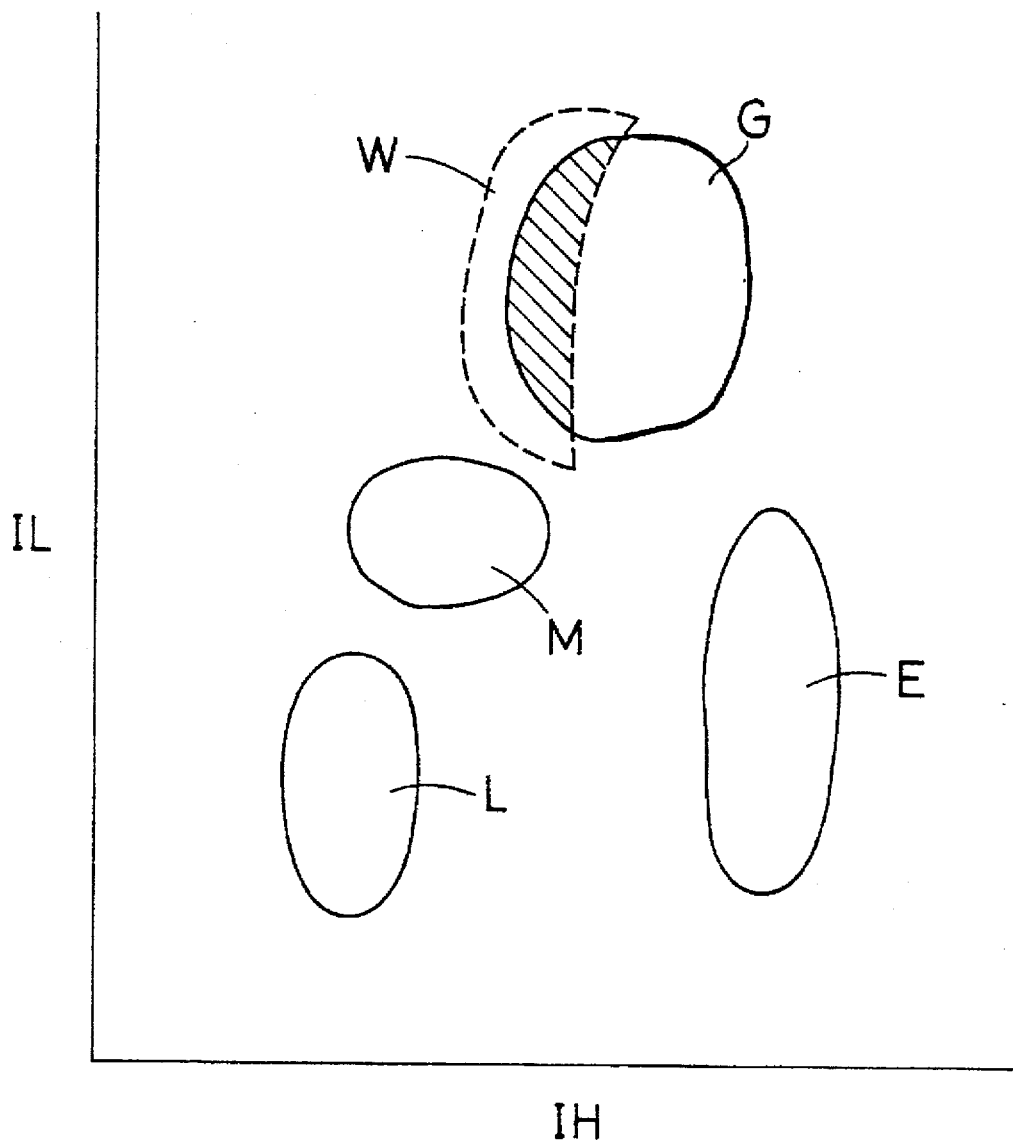
FIG. 7 is an explanatory view showing a judgement region of the preferred example according to the present invention.

Referring to FIG. 6, the region W surrounded by a broken line is an example of an abnormal-particle judgement region (hereafter referred to as "judgement region") which is set beforehand in the signal analyzer 7. (In this example, the region W is assumed to be a region where immature granulocytes appear). If the cells to be detected (immature granulocytes) appear (are plotted) in the region W as shown in FIG. 7, the signal analyzer 7 counts the number of appearing cells and, if the number exceeds a predetermined value, a message such as "POSITIVE" and a message corresponding to the appearance of the abnormal cells (immature granulocytes) are displayed in a display device 8.

Here, the judgement region may be set for blast cells, left shifts, heteromorphous lymphocytes, nucleated erythrocytes, or the like besides the above immature granulocytes, although the explanation thereof is omitted.

Accordingly, the apparatus 100 for analyzing particles makes it possible to efficiently conduct a screening test on a plurality of different specimens.

Next, a method and an apparatus for determining the judgement region will be hereafter explained.

Figure 8:
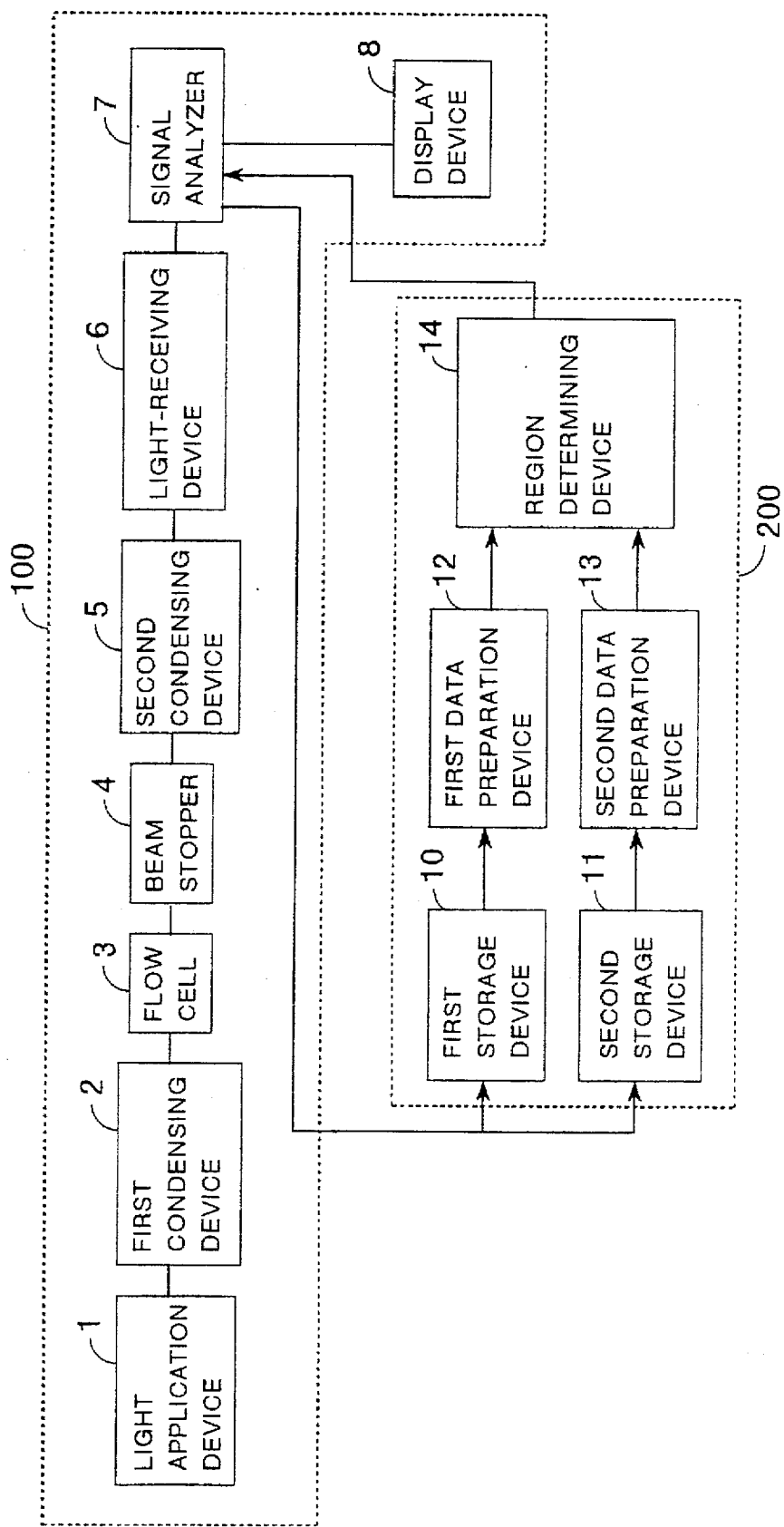
FIG. 8 is a block diagram showing an apparatus for determining a judgement region, the apparatus being applied to the preferred example of FIG. 1.

As shown in FIG. 8, an apparatus 200 for determining the particle judgement base is connected to the signal analyzer 7 in the apparatus 100 for analyzing particles. The apparatus 200 for determining the particle judgement base comprises a first storage device 10, a second storage device 11, a first data preparation device 12, a second data preparation device 13, and a region determining device 14, and is constructed with a microcomputer or a personal computer.

A plurality of normal specimens and a plurality of abnormal specimens (here, specimens in which immature granulocytes appear) are analyzed in the apparatus 100 for analyzing particles to prepare a scattergram for each.

The apparatus 200 receives the data of each scattergram from the signal analyzer 7, determines the judgement region by employing the following two methods, namely, (1) particle frequency method and (2) particle probability method, and sets the determined region in the signal analyzer 7 as shown by the region W in FIG. 6. At this time, the after-mentioned base point (region base point) for positioning the judgement region is also set in the signal analyzer 7.

(1) Particle Frequency Method

Figure 9:
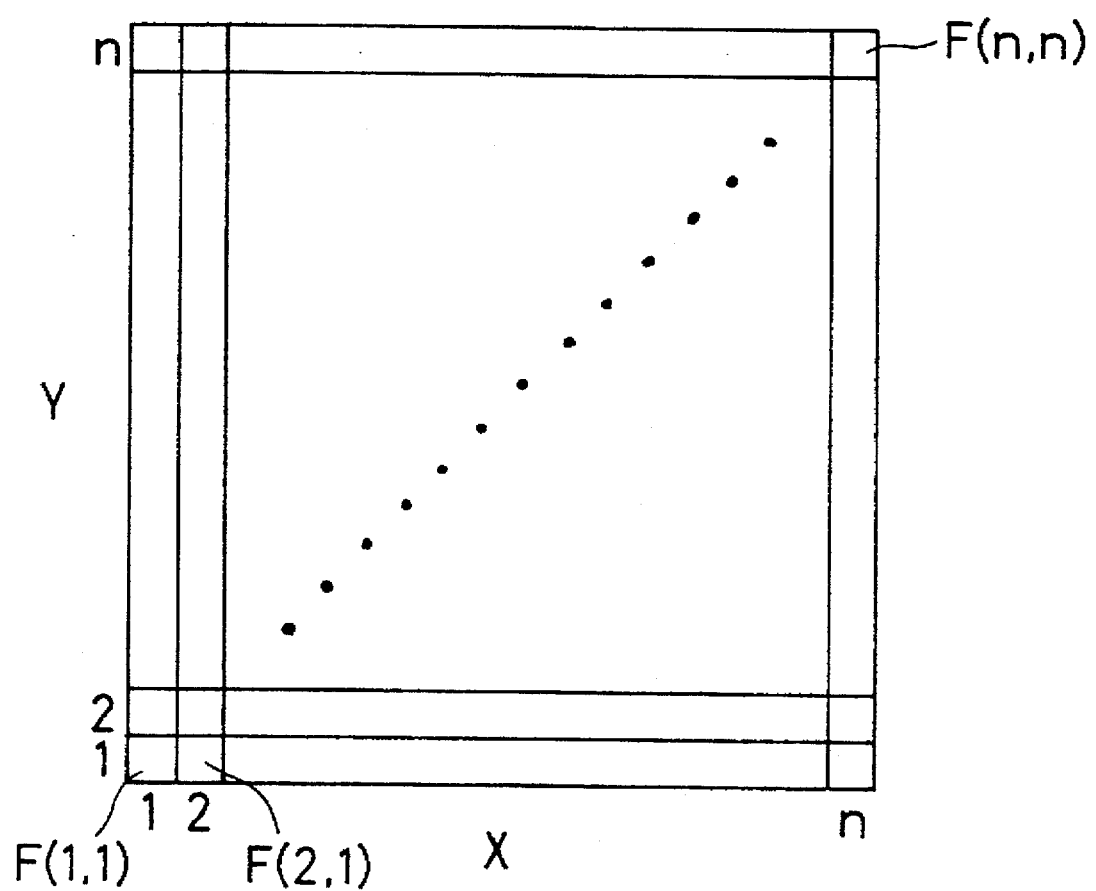
FIG. 9 is an explanatory view showing coordinates in a scattergram of the preferred example according to the present invention.

For simplicity of explanation, the coordinates (the address) (X,Y) of each dot on the plane of the scattergram shown in FIG. 5 are defined as in FIG. 9, and the frequency on each of the address is represented as $F(X,Y)$. In other words, the distribution data representing the scattergram is represented as $F(X,Y)$ (n=258, for example, in FIG. 9).

For each of N cases (for example, 200 cases) of normal specimens, a scattergram is prepared in the apparatus 100 for analyzing particles. The N distribution data $F_1(X,Y)$, $F_2(X,Y)$, ..., and $F_N(X,Y)$ shown in FIG. 10 (a) are stored in the first storage device 10 in the apparatus 200.

Next, for each of M cases (for example, 100 cases) of abnormal specimens (specimens in which immature granulocytes appear), a scattergram is prepared in the apparatus 100 for analyzing particles. The M distribution data $G_1(X,Y)$, $G_2(X,Y)$, ..., and $G_M(X,Y)$ shown in FIG. 10 (b) are stored in the second storage device 11 in the apparatus 200. The first data preparation device 12 overlappingly stacks the distribution data stored in the first storage device 10 (the frequency is added address by address), as shown in FIG. 11 (a).

Figure 12:
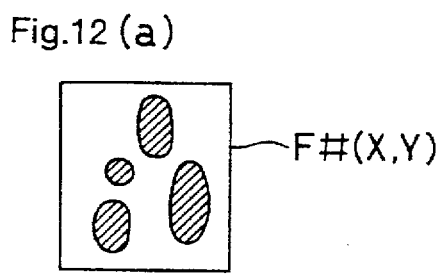
FIGS. 12 (a) and 12 (b) are explanatory views for showing a method of determining a judgement region in the preferred example according to the present invention.
Figure 12:
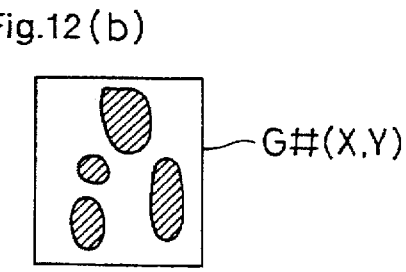

In other words, the distribution data F#(X,Y) of the basic normal scattergram is calculated from the following equation (1) as shown in FIG. 12 (a).

$$F\#(X,Y) = F_1(X,Y) + F_2(X,Y) + \ldots + F_N(X,Y) \quad (1)$$

Figure 11:
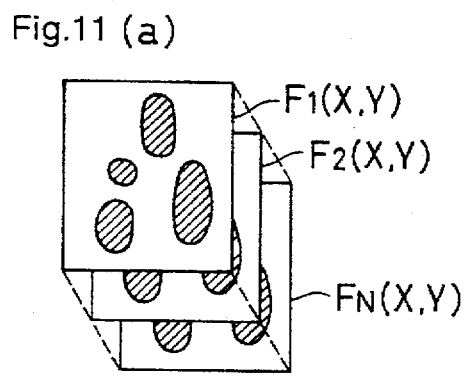
FIGS. 11 (a) and 11 (b) are explanatory views for showing a method of determining a judgement region in the preferred example according to the present invention.
Figure 11:
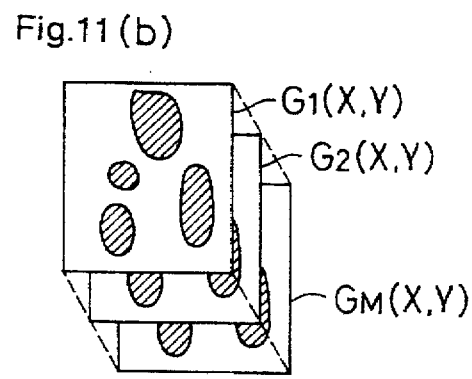

On the other hand, the second data preparation device 13 overlappingly stacks the distribution data stored in the second storage device 11 (the frequency is added address by address), as shown in FIG. 11 (b).

In other words, the distribution data G#(X,Y) of the basic abnormal scattergram is calculated from the following equation (2) as shown in FIG. 12 (b).

$$G\#(X,Y) = [G_1(X,Y) + G_2(X,Y) + \ldots + G_M(X,Y)] \cdot (N/M) \quad (2)$$

Here, the multiplier (N/M) on the right side of the equation (2) is for adjusting the number of data to be the same as in the equation (1).

If the scattergram represented by the distribution data F#(X,Y) shown in FIG. 12 (a) becomes like that of FIG. 13 (a) by including the unnecessary components such as noise, and its cross-sectional histogram has a broadened foot such as shown in FIG. 13 (b), the foot is cut off at a predetermined threshold value th1, the scattergram and the histogram being modified as shown in FIGS. 14 (a) and (b).

In other words, F#$_{th}$(X,Y) which is shown in FIG. 14 (a) and calculated by the following equation (3) becomes the distribution data of the fundamental normal scattergram.

$$F\#_{th}(X,Y) = F\#(X,Y) - th1 \quad (F\#(X,Y) > th1) \quad (3)$$
$$F\#_{th}(X,Y) = 0 \quad (F\#(X,Y) \leq th1)$$

The region determining device 14 determines the judgement region as follows.

Figure 15:
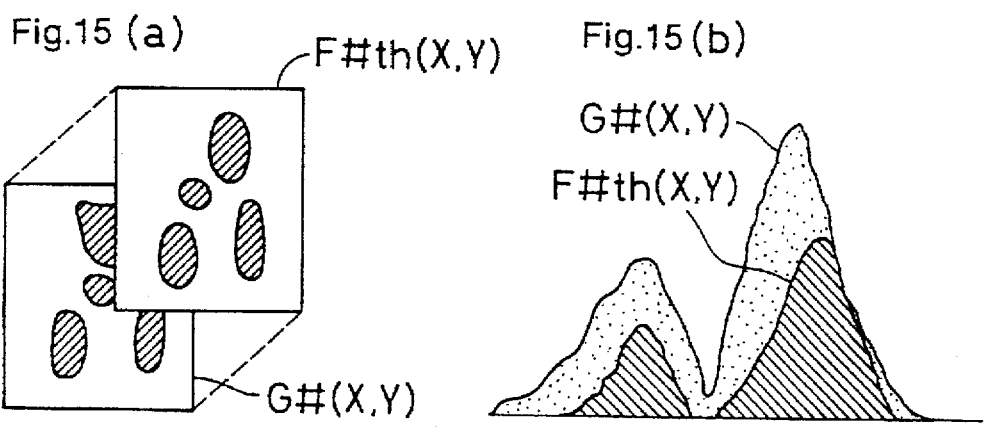
FIGS. 15 (a) and 15 (b) are explanatory views for showing a method of determining a judgement region in the preferred example according to the present invention.
Figure 16:
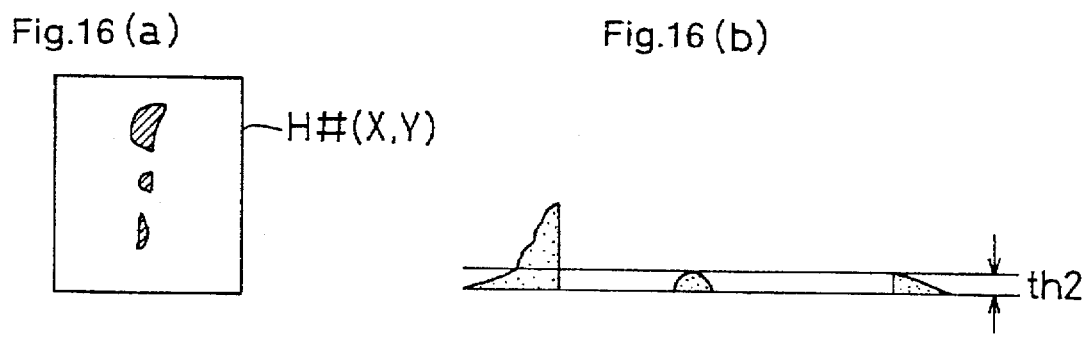
FIGS. 16 (a) and 16 (b) are explanatory views for showing a method of determining a judgement region in the preferred example according to the present invention.

First, the fundamental normal scattergram F#$_{th}$(X,Y) is cut out from the fundamental abnormal scattergram G#$_{th}$(X,Y) as shown in FIGS. 15 (a) and (b).

As a result of this, a scattergram H#(X,Y) such as shown in FIG. 18 (a) is obtained. FIG. 18 (b) shows its cross-sectional histogram. In other words, H#(X,Y) is calculated as follows.

$$H\#(X,Y) = G\#(X,Y) \quad (\text{if } F\#_{th}(X,Y) = 0) \quad (4)$$
$$H\#(X,Y) = 0 \quad (\text{if } F\#_{th}(X,Y) > 0)$$

Here, as shown in FIG. 18 (a), a plurality of regions may have been obtained. Accordingly, in order to have only one region, the foot of the histogram is cut off at a threshold value th2, as shown in FIG. 18 (b). In other words, the following operation is carried out.

$$H\#_{th}(X,Y) = H\#(X,Y) - th2 \quad (H\#(X,Y) > th2) \quad (5)$$
$$H\#_{th}(X,Y) = 0 \quad (H\#(X,Y) \leq th2)$$

Figure 17:
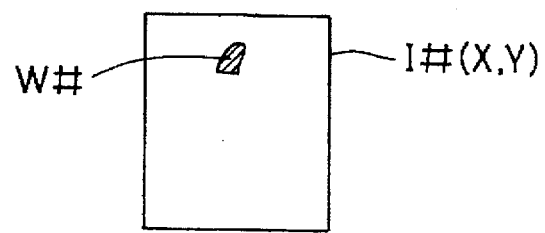
FIG. 17 is an explanatory view for showing a method of determining a judgement region in the preferred example according to the present invention.

Next, the following operation is carried out to determine a distribution data I#(X,Y) representing the judgement region W# shown in FIG. 17.

$$I\#(X,Y) = 1 \quad (H\#_{th}(X,Y) > 0) \quad (6)$$
$$I\#(X,Y) = 0 \quad (H\#_{th}(X,Y) = 0)$$

(2) Particle Probability Method

Figure 10:
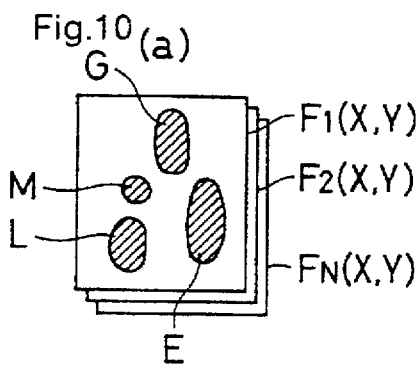
FIGS. 10 (a) and 10 (b) are explanatory views for showing a method of determining a judgement region in the preferred example according to the present invention.
Figure 10:
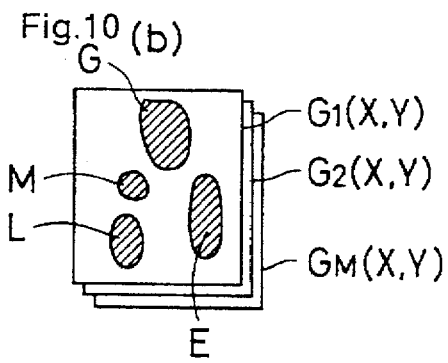

As shown above, when the distribution data of the scattergrams prepared from the normal specimens and the abnormal specimens are stored in the first storage device 10 and the second storage device 12, respectively, as shown in FIGS. 10 (a) and (b), the first data preparation device 12 and the second data preparation device 13 normalize the distribution data of each of the scattergrams using the following equation.

$$F_k\%(X,Y) = \frac{F_k(X,Y)}{\sum_{X=1}^{n}\sum_{Y=1}^{n} F_k(X,Y)} \quad (k=1,2,\ldots,N) \quad (7)$$

$$G_k\%(X,Y) = \frac{G_k(X,Y)}{\sum_{X=1}^{n}\sum_{Y=1}^{n} G_k(X,Y)} \quad (k=1,2,\ldots,N) \quad (8)$$

Here, to normalize is to calculate the ratio (%) of the number of cells (i.e. probability of appearance) at each dot in the scattergram relative to the total number of cells in the scattergram and to modify the scattergram based on the ratio.

Then, the first data preparation device 12 and the second data preparation device 13 overlappingly stack each of the distribution data (the frequency is added address by address), as shown in FIGS. 18 (a) and (b).

In other words, the distribution data F%(X,Y) of the fundamental normal scattergram and the distribution data G%(X,Y) of the fundamental abnormal scattergram are calculated from the following equations (9) and (10), respectively, as shown in FIGS. 19 (a) and (b).

$$F\%(X,Y) = F_1\%(X,Y) + F_2\%(X,Y) + \ldots + F_N\%(X,Y) \quad (9)$$

$$G\%(X,Y) = [G_1\%(X,Y) + G_2\%(X,Y) + \ldots + G_M\%(X,Y)] \cdot (N/M) \quad (10)$$

The region determining device 14 then determines the judgement region as follows. First, the distribution data G%(X,Y) of the fundamental abnormal scattergram is divided by the distribution data F%(X,Y) of the fundamental normal scattergram to give H%(X,Y) as shown in the following equation.

$$H\%(X,Y) = G\%(X,Y)/F\%(X,Y) \quad (G\%(X,Y) \geq F\%(X,Y)) \quad (11)$$
$$H\%(X,Y) = 0 \quad (G\%(X,Y) < F\%(X,Y))$$

Figure 20:
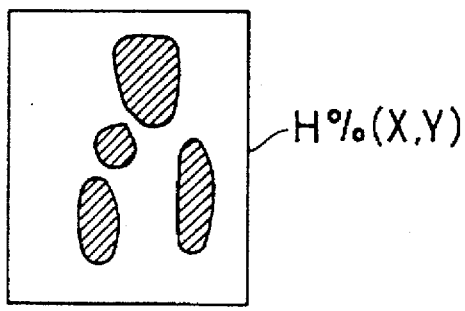
FIGS. 20 (a) and 20 (b) are explanatory views for showing a method of determining a judgement region in the preferred example according to the present invention.
Figure 20:
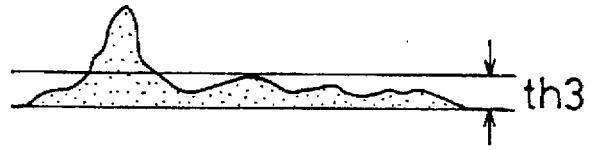

Based on the scattergram shown by H%(X,Y) in FIG. 20 (a), the foot of the histogram is cut off at a threshold value th3, as shown in FIG. 20 (b). In other words, the following operation is conducted. FIG. 20 (b) is a cross-sectional histogram of an essential part of FIG. 20 (a).

$$H\%_{th}(X,Y) = H\%(X,Y) - th3 \quad (H\%(X,Y) > th3) \quad (12)$$
$$H\%_{th}(X,Y) = 0 \quad (H\%(X,Y) \leq th3)$$

Figure 21:
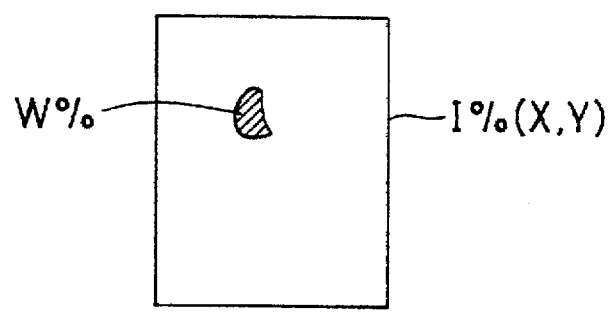
FIG. 21 is an explanatory view for showing a method of determining a judgement region in the preferred example according to the present invention.

Next, the following operation is carried out to determine a distribution data I%(X,Y) representing the judgement region W % shown in FIG. 21.

$$I\%(X,Y) = 1 \quad (H\%_{th}(X,Y) > 0) \quad (13)$$
$$I\%(X,Y) = 0 \quad (H\%_{th}(X,Y) = 0)$$

Figure 22:
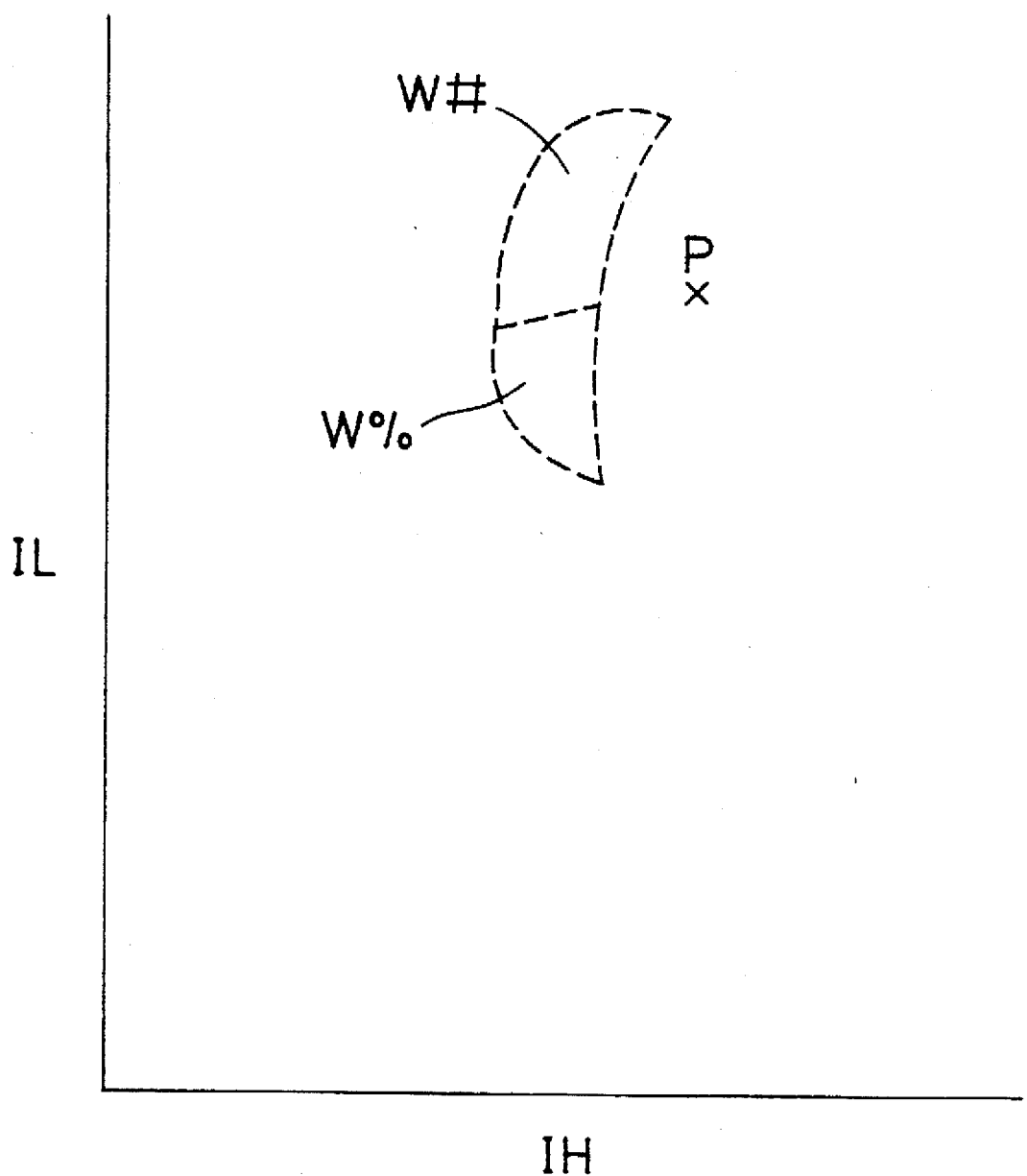
FIG. 22 is an explanatory view showing a base point of a judgement region in a scattergram of the preferred example according to the present invention.

When the region data of the judgement regions W# and W % are thus calculated, the region determining device 14 calculates the coordinates of the base point P (hereafter referred to as "region base point"), namely P(m₁, n₁), for positioning these regions as a statistical center of gravity of the group G in the scattergram obtained from the equation (1) or (3). These region data and the coordinates of the region base point are set in the signal analyzer 7 as shown in FIG. 22.

The method and the apparatus for correcting the judgement region set as above will be hereinafter explained.

FIG. 25 is a detailed block diagram of the signal analyzer 7 shown in FIG. 1. The signal analyzer 7 comprises a distribution data preparation device 31 for preparing a distribution data (distribution figure) of a scattergram upon receiving the signal from the light receiving device 6, a distribution data storage device 32 for storing the prepared distribution data, a base point extraction device 35 for extracting a group base point indicating the position of each group in the distribution data of the scattergram, a region base point storage device 33 for storing the region base point calculated by the region determining device 14, a judgement region storage device 34 for storing the judgement region determined by the region determining device 14, a shift amount calculation device 36 for calculating the shift amount of the judgement region by comparing the coordinates of the group base point and the region base point, a judgement region correction device 37 for correcting the position of the judgement region on the scattergram based on the shift amount, and an abnormality judgement device 38 for conducting a judgement on abnormality by counting the number of cells appearing in the judgement region.

Figure 23:
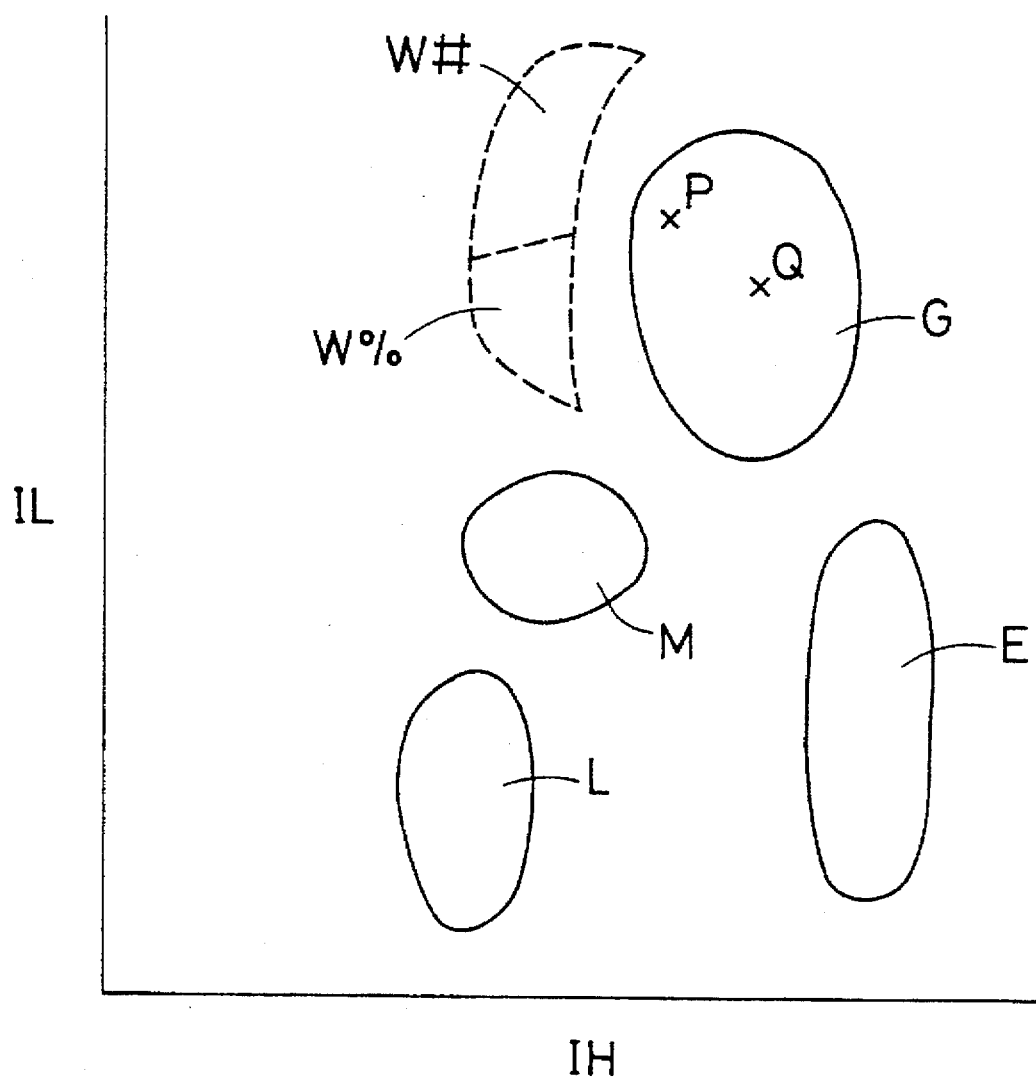
FIG. 23 is an explanatory view showing a position relationship between a judgement region and a group in a scattergram of the preferred example according to the present invention.

When one specimen to be examined is supplied to the flow cell 3, the distribution data preparation device 31 of the signal analyzer 7 prepares a scattergram based on the specimen, as shown in FIG. 23, and stores the distribution data in the distribution data storage device 32. Then, the base point extraction device 35 calculates a statistical center of gravity $Q(m_2, n_2)$ of the group G in the prepared scattergram and extracts it as the group base point.

The shift amount calculation device 36 calculates the shift amount $\Delta X = m_2 - m_1$, $\Delta Y = n_2 - n_1$ which is necessary for making the region base point $P(m_1, n_1)$ of the judgement regions W# and W % identical to the group base point $Q(m_2, n_2)$.

Figure 24:
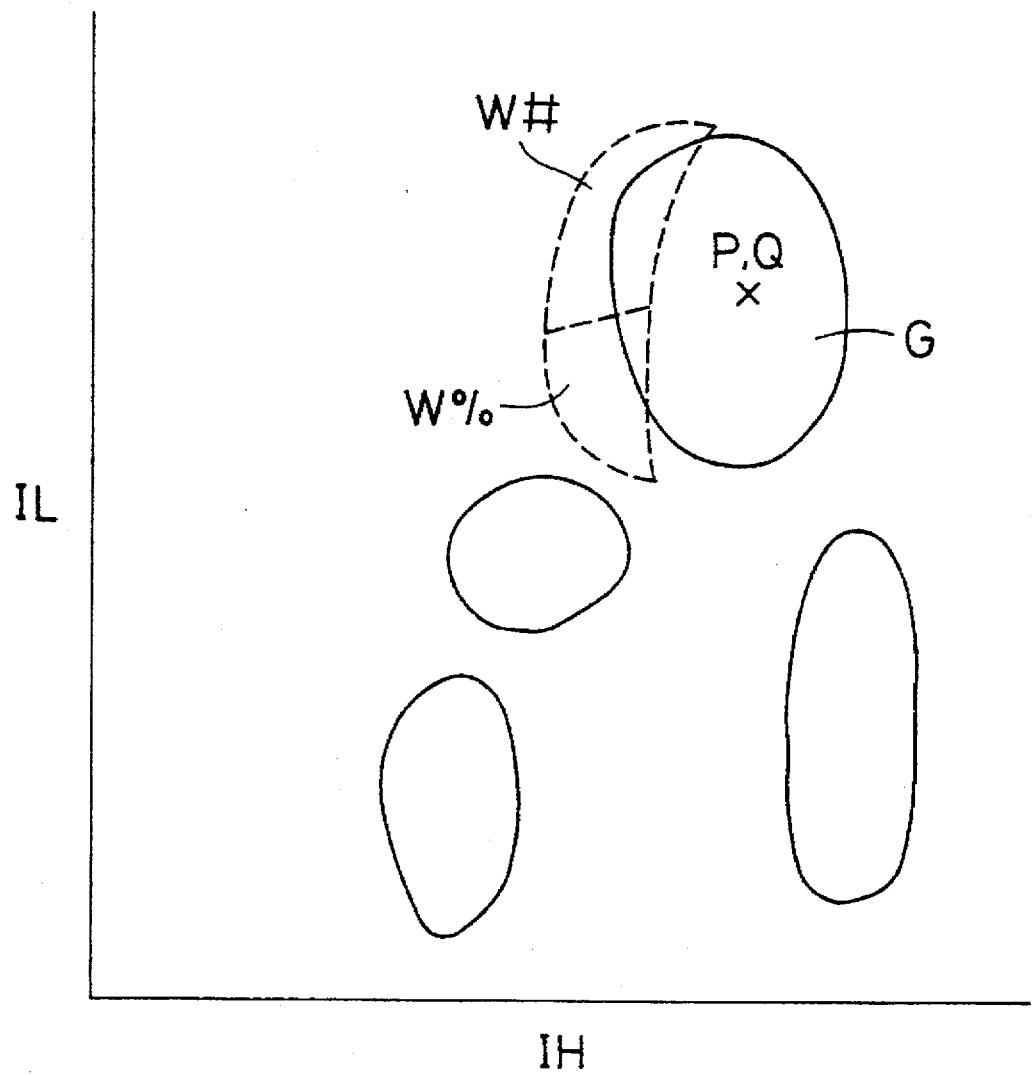
FIG. 24 is an explanatory view showing a method for correcting the position of a judgement region in a scattergram of the preferred example according to the present invention.

The judgement region correction device 37 corrects the position of the judgement regions W# and W %, as shown in FIG. 24, by transferring the judgement regions by the calculated shift amount. The abnormality judgement device 38 counts the number of cells appearing within the corrected judgement region in the scattergram and makes the display device 8 display the message corresponding to the counted number of cells.

According to the present invention, a difference in distribution data of specimen groups which belong to two kinds of categories is statistically calculated so that the region on the distribution data where peculiar particles exist, that is, the judgement region of the abnormal particles, can be determined easily and objectively.

Although the present invention has fully been described by way of example with reference to the accompanying drawings, it is to be understood that various changes and modifications will be apparent to those skilled in the art. Therefore, unless otherwise such changes and modifications depart from the scope of the invention, they should be construed as being included therein.

What is claimed is:

1. A method for determining a particle criterion to set a predetermined region as the particle criterion in distribution data of particles of a specimen to be analyzed and to analyze the specimen based on particles which appear in the predetermined region, comprising the steps of:

preparing first fundamental distribution data by accumulating each distribution data of a first specimen group which belongs to a first category;

preparing second fundamental distribution data by accumulating each distribution data of a second specimen group which belongs to a second category;

calculating a region on the distribution data where peculiar particles exist in the first or second category by comparing the first and second fundamental distribution data; and establishing the calculated region that acts as the particle criterion for the specimen to be analyzed.

2. The method as defined in claim 1, wherein the first specimen group which belongs to the first category is a normal specimen group comprising normal particles, the second specimen group which belongs to the second category is an abnormal specimen group comprising normal and abnormal particles, and the peculiar particles are the abnormal particles.

3. The method as defined in claim 1, wherein the distribution data of the particles comprises an address and frequency of each particle in a distribution chart, and the steps of preparing the first and second fundamental distribution data are performed by adding the frequency of each distribution data for each address.

4. The method as defined in claim 1, wherein the step of calculating the region on the distribution data is performed by comparing the first fundamental distribution data with the second fundamental distribution data so as to calculate, as a particle criterion, the region on the distribution data where only one of the first and second fundamental distribution data exists.

5. The method as defined in claim 1, wherein the step of calculating a region on the distribution data is performed by calculating a ratio of the first fundamental distribution data to the second fundamental distribution data and by calculating, as a particle criterion, a region on the distribution data where the ratio is greater than a predetermined value.

6. The method according to claim 1, further comprising providing a threshold for the calculated region such that the threshold calculated region is continuous.

7. The method according to claim 1, further comprising correcting a position of the judgement region.

8. The method according to claim 1, further comprising:
judging particles of a specimen which exist in the calculated region; and
analyzing the specimen in accordance with said judging.

9. A device for determining a particle criterion to set a judgement region as the particle criterion in a distribution data of particles of a specimen to be analyzed and to analyze the particles of the specimen based on particles which appear in the judgement region, comprising:

first storage means for storing each distribution data of a first specimen group which belongs to a first category;

second storage means for storing each distribution data of a second specimen group which belongs to a second category;

first data preparation means for preparing a first fundamental distribution data by accumulating each distribution data of the first specimen group;

second data preparation means for preparing second fundamental distribution data by accumulating each distribution data of the second specimen group; and region determining means for determining, as the particle criterion for the specimen to be analyzed, a region on the distribution data where peculiar particles exist in the first or second category by comparing the first fundamental distribution data with the second fundamental distribution data.

10. The device as defined in claim 9, wherein the first specimen group which belongs to the first category is a normal specimen group comprising normal particles, the second specimen group which belongs to the second category is an abnormal specimen group comprising normal and abnormal particles, and the peculiar particles are the abnormal particles.

11. The device as defined in claim 9, wherein the distribution data of the particles comprises an address and frequency of each particle in a distribution chart, and the first and second data preparation means prepare the first and second fundamental distribution data by adding the frequency of each distribution data for each address.

12. The device as defined in claim 9, wherein the region determining means calculates, as the particle criterion, a region on the distribution data where only one of the first and second fundamental distribution data exists by comparing the first fundamental distribution data with the second fundamental distribution data.

13. The device as defined in claim 9, wherein the region determining means calculates a ratio of the first fundamental distribution data to the second fundamental distribution data and determines, as the particle criterion, a region on the distribution data where the ratio is greater than a predetermined value.

14. A particle analyzer, comprising:
   judgement region storage means for storing, as a particle criterion, a region determined by the device according to claim 6;
   distribution data preparation means for measuring an optional specimen to prepare a distribution data of the specimen;
   judgement means for judging particles which exist in the determined region on the prepared distribution data; and
   output means for outputting a result obtained by the judgement means.

15. The particle analyzer according to claim 14, further comprising means for analyzing the particles in the specimen in accordance with said result.

16. A particle analyzer, comprising:
   judgement region storage means for storing, as a particle criterion, a region determined by the device according to claim 9;
   input means fop inputting a distribution data of an optional specimen;
   judgement means for judging particles which exist in the determined region with respect to the input distribution data; and
   output means for outputting a result obtained by the judgement means.

17. The particle analyzer according to claim 16, further comprising means for analyzing the particles in the specimen in accordance with said result.

18. The device as defined in claim 9, wherein said region determining means further includes means for truncating the region at a threshold such that the truncated region will be continuous.

19. The device as defined in claim 9, wherein said region determining means further includes means for correcting a position of the region.

20. The device as defined in claim 9, wherein said region determining means further includes means for determining a region base point for the region.

* * * * *